United States Patent
Gustafsson et al.

(10) Patent No.: US 10,610,703 B2
(45) Date of Patent: Apr. 7, 2020

(54) SYSTEM AND A METHOD FOR VERIFYING A TREATMENT PLAN

(71) Applicant: ScandiDos AB, Uppsala (SE)

(72) Inventors: Anders Gustafsson, Uppsala (SE); Thomas Matzen, Uppsala (SE); Erik Bängtsson, Uppsala (SE)

(73) Assignee: ScandiDos AB (SE)

( * ) Notice: Subject to any disclaimer, the term of this patent is extended or adjusted under 35 U.S.C. 154(b) by 179 days.

(21) Appl. No.: 15/742,011

(22) PCT Filed: Jun. 14, 2016

(86) PCT No.: PCT/EP2016/063638
§ 371 (c)(1),
(2) Date: Jan. 4, 2018

(87) PCT Pub. No.: WO2017/005465
PCT Pub. Date: Jan. 12, 2017

(65) Prior Publication Data
US 2018/0200537 A1    Jul. 19, 2018

(30) Foreign Application Priority Data
Jul. 8, 2015    (EP) .................................... 15175902

(51) Int. Cl.
*A61N 5/10*    (2006.01)
(52) U.S. Cl.
CPC .......... *A61N 5/1075* (2013.01); *A61N 5/1071* (2013.01); *A61N 2005/1076* (2013.01)
(58) Field of Classification Search
CPC .......... A61N 5/00; A61N 5/10; A61N 5/1075; A61N 5/1071; A61N 5/103; A61N 2005/1076; A61B 6/583
(Continued)

(56) References Cited

U.S. PATENT DOCUMENTS

| 7,945,022 B2 | 5/2011 | Nelms et al. |
| 2003/0076926 A1 | 4/2003 | Renner |
| 2010/0215147 A1* | 8/2010 | Muller ............... A61N 5/1042 378/65 |

FOREIGN PATENT DOCUMENTS

| EP | 1 917 999 A1 | 5/2008 |
| WO | WO 2008/053026 A1 | 5/2008 |

OTHER PUBLICATIONS

J. M. Kapatoes, et al. "A feasible method for clinical delivery verification and reconstruction in tomotherapy", Medical Physics, AIP, Melville, NY, US, vol. 28, No. 4, Apr. 1, 2001. pp. 528-542.

* cited by examiner

*Primary Examiner* — Jurie Yun
(74) *Attorney, Agent, or Firm* — Condo Roccia Koptiw LLP (57) ABSTRACT

The present invention relates to a method for determining an energy fluence correction in a quality assurance system for a radiation therapy apparatus, which method comprises receiving a treatment plan description; generating a set of measured phantom dose values; generating a set of determined phantom dose values, by determining phantom dose values based on at least the treatment plan description and a phantom description; determining a set of phantom dose corrections based on at least the set of determined phantom dose values and the set of measured phantom dose values; and determining an energy fluence correction based on at least the set of phantom dose corrections. It further relates to a method for determining a reconstructed patient dose distribution based on at least the energy fluence correction, a patient description, and further data related to the treatment plan description. It also relates to corresponding quality assurance and control systems.

15 Claims, 8 Drawing Sheets

(58) Field of Classification Search
USPC .................................................. 378/65, 207
See application file for complete search history.

SYSTEM AND A METHOD FOR VERIFYING A TREATMENT PLAN

CROSS REFERENCE TO RELATED APPLICATIONS

This application is the National Stage Entry under 35 U.S.C. § 371 of Patent Cooperation Treaty Application No. PCT/EP2016/063638, filed 14 Jun. 2016, which claims the benefit of European Application No. 15175902.4, filed 8 Jul. 2015, the contents of which are hereby incorporated by reference herein.

FIELD OF THE INVENTION

The present invention relates to radiation therapy dose delivery quality assurance, and more particularly to a system and a method for determining an energy fluence correction and a reconstructed patient dose distribution, in order to verify a treatment plan.

BACKGROUND OF THE INVENTION

A radiation therapy apparatus typically radiates the patient from many different angles and with many different amounts of radiation. Before actually treating a patient a treatment plan is determined, which consists of parameter settings for driving the radiation therapy apparatus in such a way that the aimed at treatment effect at a target volume of the patient is achieved. More particularly, the treatment plan is aiming at obtaining the correct dose distribution, and thereby the correct radiation doses at the correct portions of the body of the patient, as prescribed by the physician prescribing the treatment. In other words, a high enough dose is desired in the target volume in combination with as small dose as possible in critical organs. There are many variables which affect the amount of energy that actually is absorbed in the target volume of the patient, and several thereof are not possible to determine accurately, but instead approximating models of them are used. For instance, the determination of the treatment plan can be based on a model of the radiation energy emitted by the radiation therapy apparatus at different settings, a model of how the radiation beams penetrate the body tissue, a description of the patient volume geometry, etc. In order to verify the correctness of the treatment plan, a quality assurance (QA) system is used. The QA system often includes a phantom, which is used for simulating the body of the patient and which is provided with detectors measuring actual doses at positions of the phantom corresponding to the target volume of the body that the treatment is aiming for. If the QA system indicates significant deviations from the desired doses, the treatment plan can be adjusted accordingly.

An example of a known method for determining a patient dose distribution, i.e. the distribution of the radiation dose within the body of the patient, and verifying it, is disclosed in U.S. Pat. No. 7,945,022, where the patient dose distribution is determined by means of phantom dose measurements, and the patient geometry. More particularly, a phantom dose distribution measured by means of detectors at the phantom is compared with a theoretically determined phantom dose distribution, which has been determined by the treatment planning system (TPS). The difference is used for generating a reconstructed patient dose distribution.

The prior art according to U.S. Pat. No. 7,945,022 has the drawback that it is a perturbation method and is hence limited to handle only a small dose deviation correctly. Errors that can be detected in the phantom are classified based on their magnitude into 1) perturbations, i.e. minor disturbances, and 2) "binary" errors, i.e. errors that might or might not be present. Perturbations are exemplified as modelling errors, leaf sequence errors, and the like, whereas binary errors are said to be the selection of incorrect TPS plan file or alignment errors. The idea is that the binary errors will show directly in the measurements and it is hence not meaningful to try to correct the theoretical TPS dose when these errors are present.

While in U.S. Pat. No. 7,945,022 the errors are described as either minor or binary, in the clinical reality there will always be errors that reside in the transition region between two extremes. In this region it is impossible to tell whether the magnitude of the discovered errors in the patient geometry reflects the magnitude of the measured deviations, or if the errors are amplified because the measured dose deviations are too large to fit within the class of minor errors.

Another drawback of the method discloses in U.S. Pat. No. 7,945,022 has to do with its ability to cope with modern rotational therapies, such as arc or helical therapies. The method is based on the construction of error kernels from measured and predicted (TPS) dose in the phantom and the transfer of said dose error kernels from the source of radiation to the patient volume. In order to do this transfer correctly, the position of the source, and hence the angle of beam incidence, that corresponds to a certain dose error kernel, must be known. For rotational therapy, this can only be done when either the TPS dose in the phantom is known on a sub-beam level where the gantry angle is known, or when the spatial distribution of the detectors at the phantom is such as it is possible to determine the gantry angle from which the vast majority of the dose in a detector was delivered.

SUMMARY OF THE INVENTION

It would be advantageous to provide a solution which at least reduces the above-mentioned problems with the prior art.

To better address this concern, in a first aspect of the invention there is presented a method for determining an energy fluence correction in a quality assurance system for a radiation therapy apparatus, comprising:
  receiving a treatment plan description;
  generating a set of measured phantom dose values;
  generating a set of determined phantom dose values, by determining phantom dose values on basis of at least the treatment plan description and a phantom description;
  determining a set of phantom dose corrections on basis of at least the set of determined phantom dose values and the set of measured phantom dose values; and
  determining an energy fluence correction on basis of at least the set of phantom dose corrections.

According to this method no assumptions about the magnitude of the errors have been made, but an energy fluence correction is determined, which is general as to the magnitude of the errors, and which, in turn, is useful for a proper determination of a reconstructed dose distribution.

In a second aspect of the invention there is presented a method for determining a reconstructed patient dose distribution, which comprises the above-mentioned energy fluence correction, and which further comprises:

determining a reconstructed patient dose distribution on basis of at least the energy fluence correction, a patient description, and further data related to the treatment plan description.

The resulting reconstructed dose distribution reflects the deviations in the measurements and is itself a measure of how well the treatment plan would work.

In accordance with an embodiment of the method for determining an energy fluence correction, it further comprises receiving, at the quality and assurance system, a set of treatment planning system phantom dose values, determined by the treatment planning system. The determination of a set of phantom dose corrections is further based on the set of treatment planning system phantom dose values.

In accordance with an embodiment of the method for determining an energy fluence correction, the determination of a set of phantom dose corrections comprises:
  determining a first set of phantom dose differences on basis of the set of determined phantom dose values and the set of measured phantom dose values;
  determining a second set of phantom dose differences on basis of the set of determined phantom dose values and the set of treatment planning system phantom dose values; and
  combining the first set of phantom dose differences with the second set of phantom dose differences.

Thereby, errors TPS dose engine, i.e. the algorithm for calculating dose values in the TPS, can be detected.

In accordance with an embodiment of the method for determining an energy fluence correction, the operation of generating a set of determined phantom dose values comprises determining an energy fluence on basis of the treatment plan description; and using the energy fluence for the determination of the phantom dose values.

In accordance with an embodiment of the method for determining an energy fluence correction, the energy fluence correction is generated by means of an inverse dose calculation.

In accordance with an embodiment of the method for determining a reconstructed patient dose distribution, the operation of determining a set of patient dose corrections comprises:
  determining an energy fluence on basis of said treatment plan description, wherein said further data related to the treatment plan description comprises the energy fluence.

In accordance with an embodiment of the method for determining a reconstructed patient dose distribution, said operation for determining a reconstructed patient dose distribution comprises:
  determining a corrected energy fluence by means of the energy fluence correction and the energy fluence; and
  determining the reconstructed patient dose distribution by means of the corrected energy fluence and the patient description.

Thereby, a dose distribution in the patient geometry reconstructed from measurements in a QA phantom has been advantageously obtained.

In accordance with an embodiment of the method for determining a reconstructed patient dose distribution, said operation for determining a reconstructed patient dose distribution comprises:
  determining a set of patient dose corrections on basis of at least the energy fluence correction and the patient description;
  receiving said further data related to the treatment plan description in the form of a treatment planning system patient dose distribution;
  determining the reconstructed patient dose distribution on basis of at least the treatment planning system patient dose distribution and the set of patient dose corrections.

Thereby, an absolute correction of the TPS patient dose distribution is provided.

In accordance with an embodiment of the method for determining a reconstructed patient dose distribution, said operation for determining a reconstructed patient dose distribution comprises:
  determining a patient dose distribution on basis of the energy fluence and the patient description, wherein said further data related to the treatment plan description comprises the patient dose distribution;
  determining a set of patient dose corrections on basis of the energy fluence corrections and the patient description;
  determining a set of relative patient dose corrections on basis of the patient dose distribution and the set of patient dose corrections;
  receiving a treatment planning system patient dose distribution, wherein said further data related to the treatment plan description comprises the treatment planning system patient dose distribution; and
  determining the reconstructed patient dose distribution on basis of the set of relative patient dose corrections, and the treatment planning system patient dose distribution.

Thereby, a relative correction of the TPS patient dose distribution is provided.

In accordance with an embodiment of the method for determining a reconstructed patient dose distribution, the set of patient dose corrections constitutes a dose correction distribution in the patient geometry, the patient dose distribution constitutes an ideal dose distribution in the patient geometry, and the set of relative patient dose corrections constitutes a relative dose correction in the patient volume.

According to a further aspect of the present invention, there is provided a quality assurance system for a radiation therapy treatment apparatus, comprising:
  a phantom to simulate a radiation therapy treatment, which phantom is provided with radiation detectors; and
  a computing device;
  wherein the computing device comprises:
  a measuring module connected with the radiation detectors;
  an input data device; and
  an output data device,
  wherein the input data device is arranged to receive a treatment plan description;
  wherein the measuring module is arranged to generate a set of measured phantom dose values;
  wherein the computing device is arranged to:
  generate a set of determined phantom dose values, by determining phantom dose values on basis of at least the treatment plan description and a phantom description;
  determine a set of phantom dose corrections on basis of at least the set of determined phantom dose values and the set of measured phantom dose values;
  determine an energy fluence correction on basis of at least the set of phantom dose corrections.

According to an embodiment of the quality assurance device, the computing device is arranged to determine a reconstructed patient dose distribution on basis of at least the energy fluence correction, a patient description, and further data related to the treatment plan description; and wherein the output data device is arranged to output the reconstructed patient dose distribution.

According to a further aspect of this invention, there is provided a control system for a radiation therapy treatment apparatus. The control system comprises a treatment planning system and a quality assurance system as mentioned above.

According to a further aspect of this invention, there is provided a computer program product comprising computer readable program portions for executing the operations of the method according to the above-described embodiments.

BRIEF DESCRIPTION OF THE DRAWINGS

The invention will now be described in more detail and with reference to the appended drawings in which.

DESCRIPTION OF EMBODIMENTS

Figure 1:
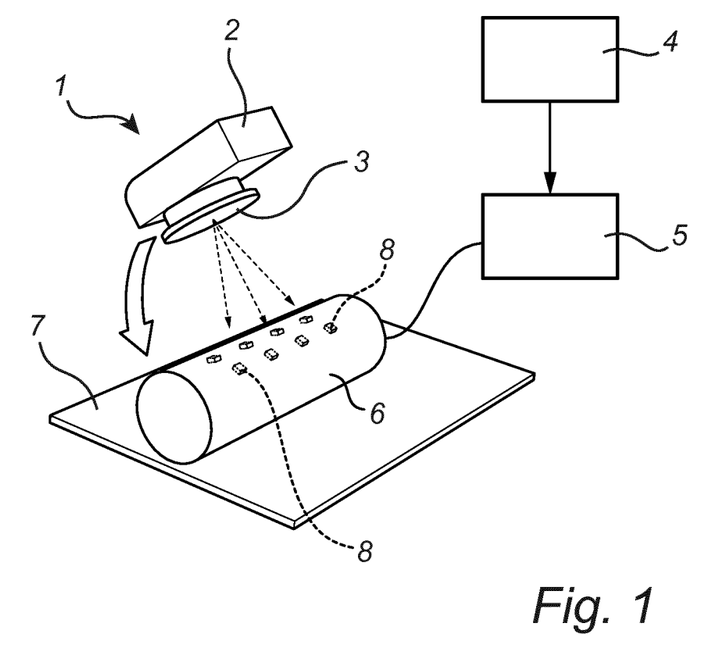
FIG. 1 schematically illustrates an example of a general radiation therapy treatment apparatus, which can be used for performing the method in accordance with the present invention, and which can be equipped with the systems according to the invention.

A typical radiation therapy apparatus 1, which can be of any suitable kind as understood by the person skilled in the art, comprises a movable gantry 2, a radiation generator 3, arranged at the gantry 2, a TPS 4, and a QA system, including a computing device 5 and a phantom 6 used for simulating the treatment of a patient. The phantom 6 is arranged on a patient bed 7, in place of the patient, during a pre-treatment phase where the treatment plan is set and validated by means of the QA system 5, 6. The gantry 2 is typically rotatable around the phantom/patient, as schematically indicated by arrows in FIG. 1. Radiation detectors 8, most schematically illustrated as simple dots, are mounted at the phantom 6, typically within the phantom but surface mounting can occur as well.

The present invention involves different methods, which are however dependent on each other. More particularly, a basic method is a method for determining an energy fluence correction, which in turn constitutes a part of a method for determining a reconstructed patient dose distribution. The method for determining the reconstructed patient dose distribution is a method for verifying the correctness of the treatment plans, i.e. for determining whether the desired dose distribution in the patient will be achieved.

Figure 2:
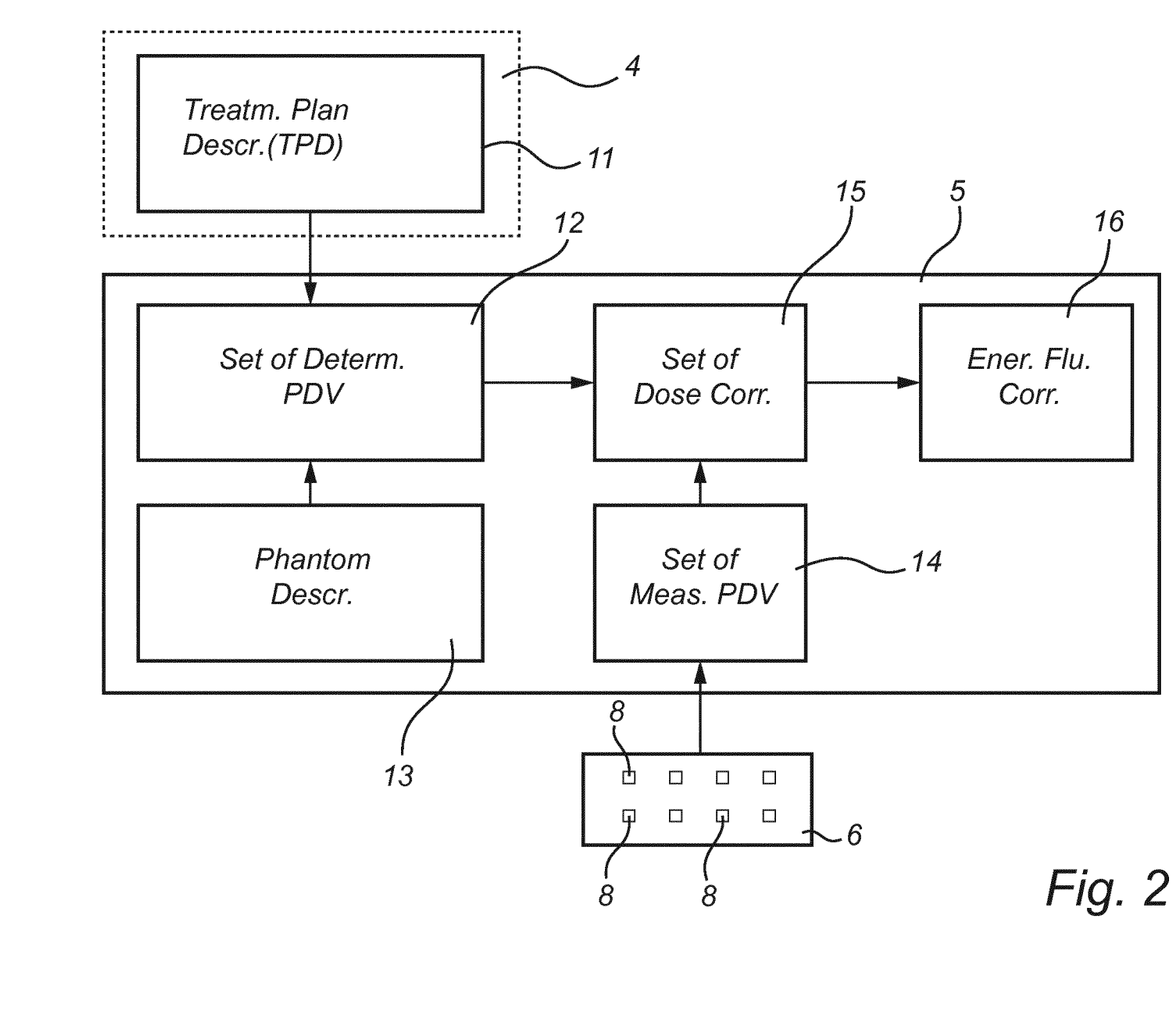
FIG. 2 illustrates an embodiment of the method according to the present invention.
Figure 3:
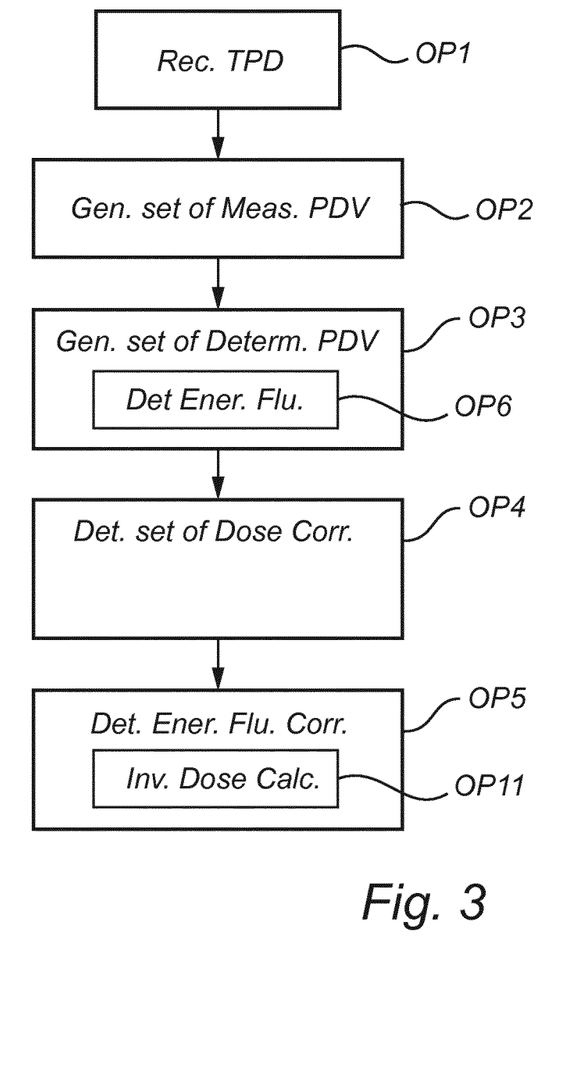
FIGS. 3 to 8 illustrate further embodiments of the method by means of flow charts.
Figure 4:
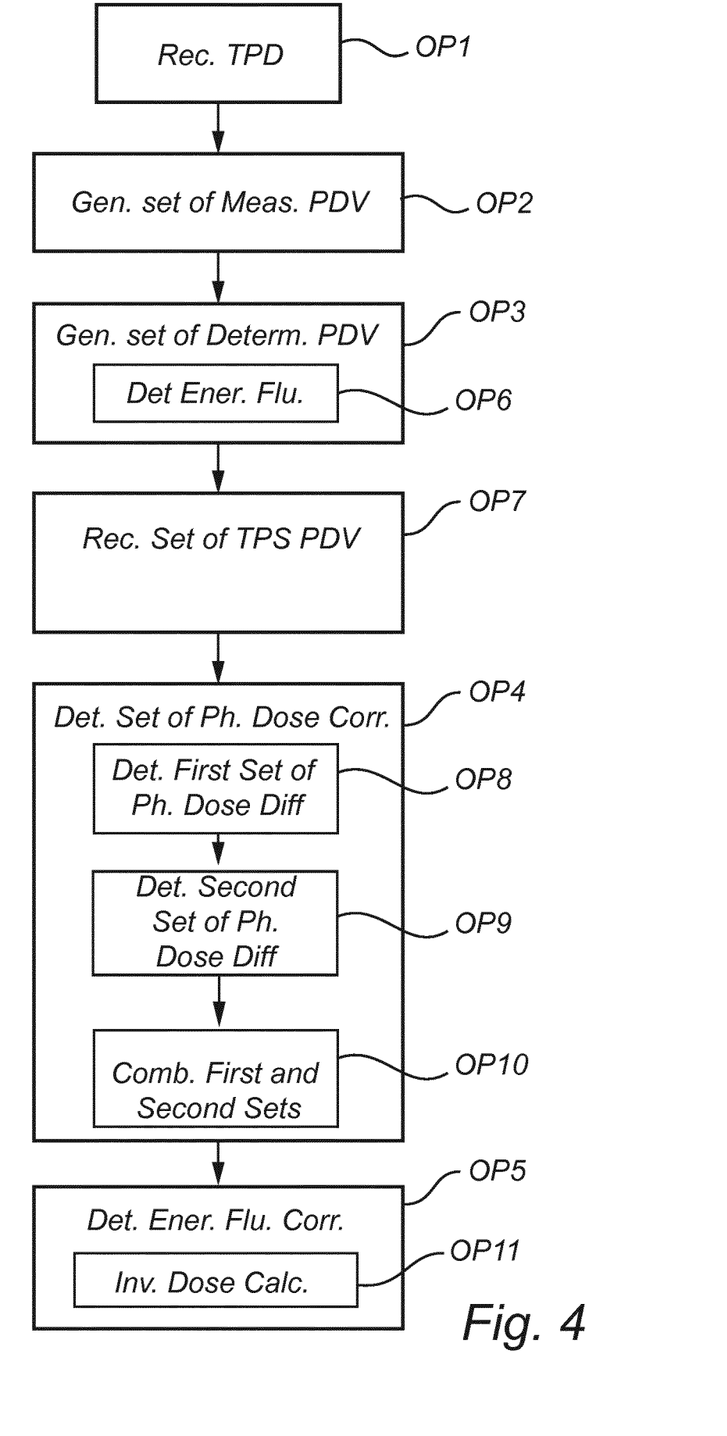

An embodiment of the method for determining an energy fluence correction in a quality assurance system for radiation therapy is illustrated in FIG. 2, which is related to both the flow of operations of the method and parts of the QA system 5, 6. Additionally, flow charts in FIGS. 3-8 illustrate different embodiments of the present methods. A general embodiment of the method for determining an energy fluence correction comprises the operation of receiving a treatment plan description 11, typically from the TPS 4, although it can be received from some other source as well, see OP1 in FIG. 3. The treatment plan description 11 is used for generating a set of determined phantom dose values (PDV) 12, OP3, by means of additional data in the form of a phantom description 13, which has been input to the QA system, and more particularly to the computing device 5. A set of measured phantom dose values 14 is generated, OP2. Typically the measured phantom dose values are generated by treating the phantom 6 according to the treatment plan description 11 and performing measurements by means of the radiation detectors 8 during that treatment. However, as an alternative, the phantom can be virtual, which means that measurements are performed by means of the radiation detectors 8 downstream of the radiation generator 3, and then the measured values are transformed to the dose values they would have caused in a phantom. A set of phantom dose corrections 15 is then determined, OP4, on basis of the set of determined phantom dose values 12 and the set of measured phantom dose values 14. Then, an energy fluence correction 16 is determined, OP5, on basis of the set of phantom dose corrections 15.

On a more detailed level, the method of determining an energy fluence correction can be performed in different ways. According to an embodiment, which is here called the direct energy fluence correction, the operation of generating a set of determined phantom dose values comprises a determination of an energy fluence on basis of the treatment plan description, OP6, and the determined phantom dose values are determined by means of that energy fluence and the phantom description. Furthermore, the determination of the energy fluence correction can be made by means of an inverse dose calculation. The energy fluence, which can be called an ideal energy fluence, is determined by means of an energy fluence calculation routine. This ideal energy fluence is used to predict the phantom dose measurements. Since the phantom geometry is known, and represented by the phantom description 13, the prediction can be done by a call to a phantom dose calculation routine that is implemented in the computing device 5 of the QA system 5, 6. This phantom dose calculation routine takes the ideal energy fluence as input, and produces an ideal phantom dose distribution in the regions of the phantom 6 where the dose was measured. For example, if the dose is measured in diodes or ionization chambers, the dose is predicted in the effective point of measurement. If the measurement is done in film, the dose is calculated in a two-dimensional plane in space.

The set of measured phantom dose values and the set of determined phantom dose values, which can be regarded as a prescribed ideal phantom dose, are compared and the difference between the dose distributions, i.e. the set of phantom dose corrections, which consequently is a set of phantom dose differences, is used to determine the requested energy fluence correction. This is done as an inverse dose calculation, where the input is the first set of phantom dose differences and the result is the requested energy fluence correction. The inverse dose calculation is performed as an iterative procedure, where an amended energy fluence input is tried for calculating the dose again and again until the calculated dose distribution is close enough to the measured dose distribution.

For most TPS, the control point level, or segment level, is the lowest level on which the dose calculation properties are exported and hence available in the treatment plan description. Consequently, it is natural to calculate the energy fluence correction on this level. But the invention is not limited to this. As long as it is possible to determine the necessary dose calculation properties on any level in the treatment plan, and measure the corresponding QA phantom dose, the invented method applies. Below are a number of examples included as a means to clarify the notion of treatment plan levels. Please observe that these examples only serves as tool to improve understanding and that they by no means implies a limitation of the scope of this invention.

One example is the situation where the number of control points or segments for a beam is very large. Then it is possible to aggregate a consecutive number of control points/segments into an agglomerate as a means to decrease the computational load of the method. The energy fluence correction is then calculated for the agglomerate, and eventually summed to form an energy fluence correction for the entire beam.

Another example is when the time resolution of the QA measurement system is lower than the time it takes to deliver a control point. Then it is necessary to determine the dose calculation properties in time frames that match the time frames of the QA measurement system. It can be necessary to find the dose calculation properties for fractional control points, that is, for instance every 0.707 control point or 3.14 control points.

The QA measurement system typically has a time resolution limit, and the timescale of this limit is the lower limit on the treatment plan levels. On this time scale, determined by the QA measurement system, the invention also applies as long as it is possible to determine the dose calculation properties for each such time intervals, or an aggregation or fraction of them. Note that an aggregate does not need to consist of an integer number of those time intervals. The size of the atomic time scale depends on the QA measurement system, and it might be a dose package, a dose pulse or a time unit that the system integrates the measurements over.

For the purposes of this application, a subbeam will denote a set of machine properties that are required to calculate the dose at a given time and treatment plan level. The dose calculation properties for a subbeam can come from a single control point, an aggregation of control points, or from an arbitrary level above or below the control point level.

An aspect of this invention is to reconstruct a patient dose distribution from the phantom dose measurements. The reconstructed dose and the TPS patient dose are likely to differ, and these deviations originate in different sources, such as plan delivery errors and dose modelling errors in the TPS and the QA system dose calculation algorithms, etc. As a means to improve the understanding of the origin of the dose deviations another embodiment of the method for determining an energy fluence correction is provided as follows. This embodiment can be regarded as a dual dose difference energy fluence correction determination.

According to this embodiment phantom device values are measured as well as determined like in the above-described embodiment. However, additionally, a set of treatment planning system phantom dose values is received, OP7, i.e. phantom dose values which have been determined by the TPS. Furthermore, the operation of determining a set of phantom dose corrections comprises determining a first set of phantom dose differences on basis of the set of determined phantom dose values and the set of measured phantom dose values, OP8; determining a second set of phantom dose differences on basis of the set of determined phantom dose values and the set of treatment planning system phantom dose values, OP9; and combining the first set of phantom dose differences with the second set of phantom dose differences, OP10. As in the previously described embodiment, the set of determined phantom dose values, which is a distribution, is determined on an appropriate subbeam level. The determinations of the phantom dose differences, or distributions, and the combination of them, are then performed on the same subbeam level.

The obvious choice for the combination is to simply add the first and second sets of phantom dose differences, but any kind of combination of the sets may apply. Examples of possible schemes for combinations are weighting of the distributions with (different) constants,
weighting of the distributions with some function in order to enhance the importance of certain phantom regions for the energy fluence reconstruction,
taking the mean of the dose distributions, etc.

These examples are for illustrational purposes only and do not impose any limitation of the scope.

The result of the combination is then used as input to an inverse dose calculation method provided in the QA system and the result of the inverse dose calculation is the requested energy fluence correction.

If the energy fluence correction resulting from the dual dose difference energy fluence correction determination is overall of small magnitude, this indicates either that the two dose differences contradict each other, or that both differences are small. Similarly, if the dual dose difference energy fluence correction is of substantial magnitude it is not possible to tell if one of the contributions is negligible, and the other is substantial, if it is vice versa, or if both energy fluence corrections are of "half-substantial" magnitude. In order to settle this issue, the dual dose difference energy fluence correction must be compared with the direct energy fluence correction.

If the two corrections coincide, the contribution from errors in the TPS dose calculation algorithm is negligible. But on the other hand, if the dual dose difference energy fluence correction is much larger than the direct energy fluence correction, the contribution from errors in the TPS phantom dose calculation is substantial. This is the strength of the dual dose correction method, that it gives a tool that can be used to detect mistakes in the TPS dose calculation algorithm.

The energy fluence correction methods can be used in the following ways to calculate a reconstructed patient dose distribution in the patient geometry.

Figure 5:
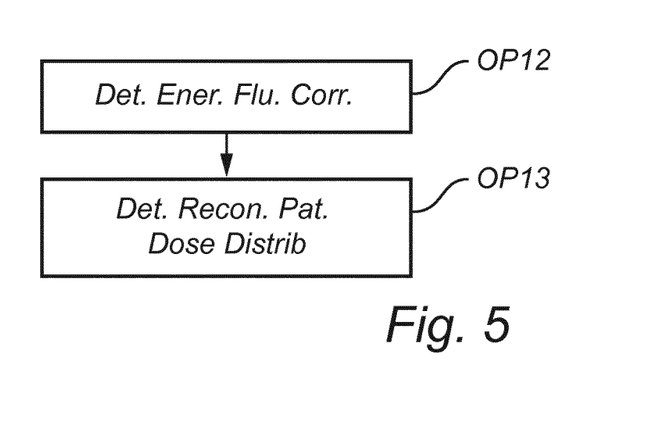
Figure 6:
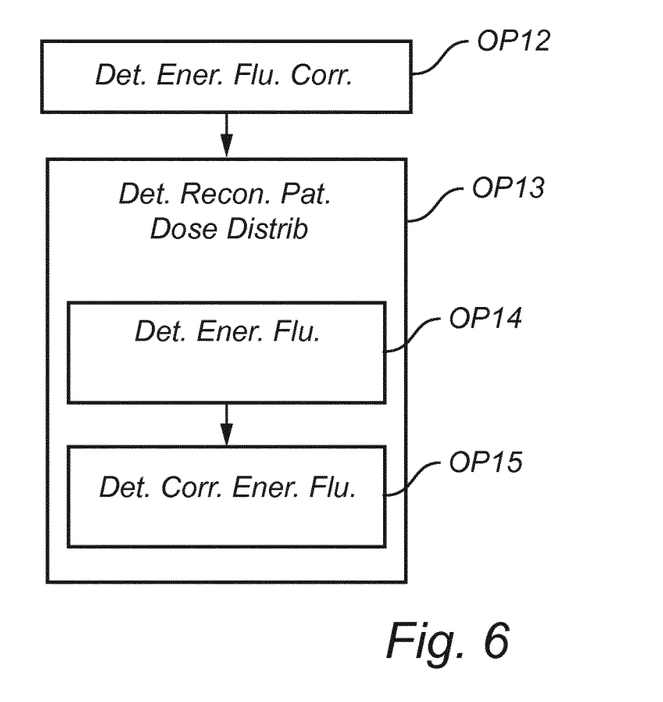
Figure 7:
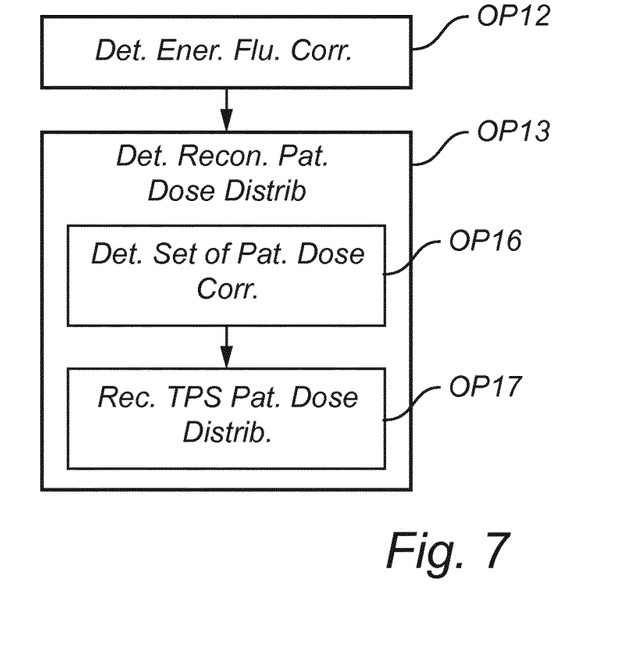

Generally described, as illustrated with the flow chart of FIG. 5, the energy fluence correction is determined by means of any one of the above-described methods, OP12, and a reconstructed patient dose distribution is determined, OP13, on basis of at least the energy fluence correction, a patient description, and further data related to the treatment plan description.

In accordance with a more detailed embodiment of the method the operation of determining the reconstructed patient dose distribution, OP13, comprises determining an energy fluence on basis of the treatment plan description, OP14. Here the aforementioned further data related to the treatment plan description comprises this energy fluence. Then a corrected energy fluence is determined by means of the energy fluence correction and the energy fluence, OP15. The reconstructed patient dose distribution is thus determined by means of the corrected energy fluence and the patient description. The energy fluence can be seen as an ideal energy fluence, and is determined on a subbeam level. In practise, the energy fluence has already been calculated in conjunction with the determination of the energy fluence correction, and is merely read from a storage. The result of the determination of a reconstructed patient dose distribution is a dose distribution in the patient geometry that is reconstructed from measurements in a QA phantom.

The TPS patient dose distribution is, as described above, in most cases not available on levels lower than beam or plan level. Therefore, typically, the reconstructed subbeam dose distribution must be summed together over a beam or the entire treatment plan in order to achieve a patient dose distribution that is meaningful to compare to the TPS patient dose distribution.

The reconstructed patient dose and the TPS dose most likely differ due to a number of reasons. These deviations originate, as is pointed out in U.S. Pat. No. 7,945,022, in two classes of errors, delivery errors and dose modelling errors. To the first class belong errors that occur during the delivery of the treatment plan such as the treatment head and/or the collimating devices may be out of position, the phantom may be positioned on the couch with an offset with respect to the expected position, etc. For dynamic therapy the collimating devices are in motion during the entire treatment and this gives rise to motion blur in the measurements. This is just a subset of delivery errors and the list can be much longer.

The class of dose modelling errors contains all the errors that originate in the calculation of the dose that is delivered to the patient. These errors may be due to sheer implementation mistakes in the TPS and the QA system ("bugs") and due to wrong input data to the dose engine (wrong patient description, wrong treatment plan description, wrong machine properties, etc.), and due to different dose models. Errors with the origin in the first two sources are in general unknown, and remain so until they give rise to large enough deviations between the calculated and the measured dose.

When it comes to the dose modelling errors that are due to the selection of different dose models in the TPS and in the QA software the reasons are somewhat different. Both the TPS dose distribution and the QA system dose distribution are calculated with dose engines that employ a dose model in order to describe how the energy is transported through the patient. These dose models are based on approximations of the dose transportation physics and are thus bound to introduce deviations from the actual dose. Although the properties of these approximations are well known, it is in general not an easy task to judge how they will affect the dose distribution in a complex patient geometry. It shall also be stated here that since the dose model errors are approximation errors, they are in general smaller than both implementation errors and errors due to bad input to the dose engine.

Common dose models, e.g. PB (Pencil Beam), CC (Collapsed Cone) and MC (Monte Carlo), all have their advantages and disadvantages. Which model that is used in a dose engine is a matter of implementation complexity, computational effort, state of the art when the dose calculation was implemented, etc. Even if the TPS and the QA system use the same dose model, differences in the implementation of the two systems are likely to lead to differences in the resulting dose distributions.

An observation regarding all these different deviations that is made in U.S. Pat. No. 7,245,022 leads to the conclusion that for a reconstructed patient dose that is calculated by the algorithm described above, it is difficult to distinguish between the delivery errors and errors due to the dose modelling errors. To address this issue, two further embodiments of the method for reconstructing the patient dose are provided. They can be referred to as TPS patient dose distribution with absolute correction and TPS patient dose distribution with relative correction.

In the embodiment determining a patient dose distribution with absolute correction, the starting point is the determination of the energy fluence correction. As in the above embodiment, the energy fluence correction can be calculated using any of the embodiments of the methods for determining an energy fluence correction as described above.

The operation of determining a reconstructed patient dose distribution comprises determining a set of patient dose corrections on basis of at least the energy fluence correction and the patient description, OP16; receiving said further data related to the treatment plan description in the form of a treatment planning system patient dose distribution (TPS PDD), OP17; and determining the reconstructed patient dose distribution on basis of at least the TPS PDD and the set of patient dose corrections. The thereby resulting dose distribution is the patient dose distribution with absolute correction. To be fully clear, it should be noted that the treatment planning system patient dose distribution is the patient dose distribution determined by the treatment planning system on basis of the treatment plan.

In the typical scenario, the dose correction is of much smaller magnitude than the TPS dose. Hence, the errors due to differences in dose algorithm implementation and dose models are relatively small, and the deviations in the two dose distributions should to a large extent originate in the phantom dose measurements.

The absolute dose correction is calculated on subbeam level and the contributions are summed together to a level where the comparison with the TPS dose distribution is relevant. In most cases, that is on beam or plan level.

Figure 8:
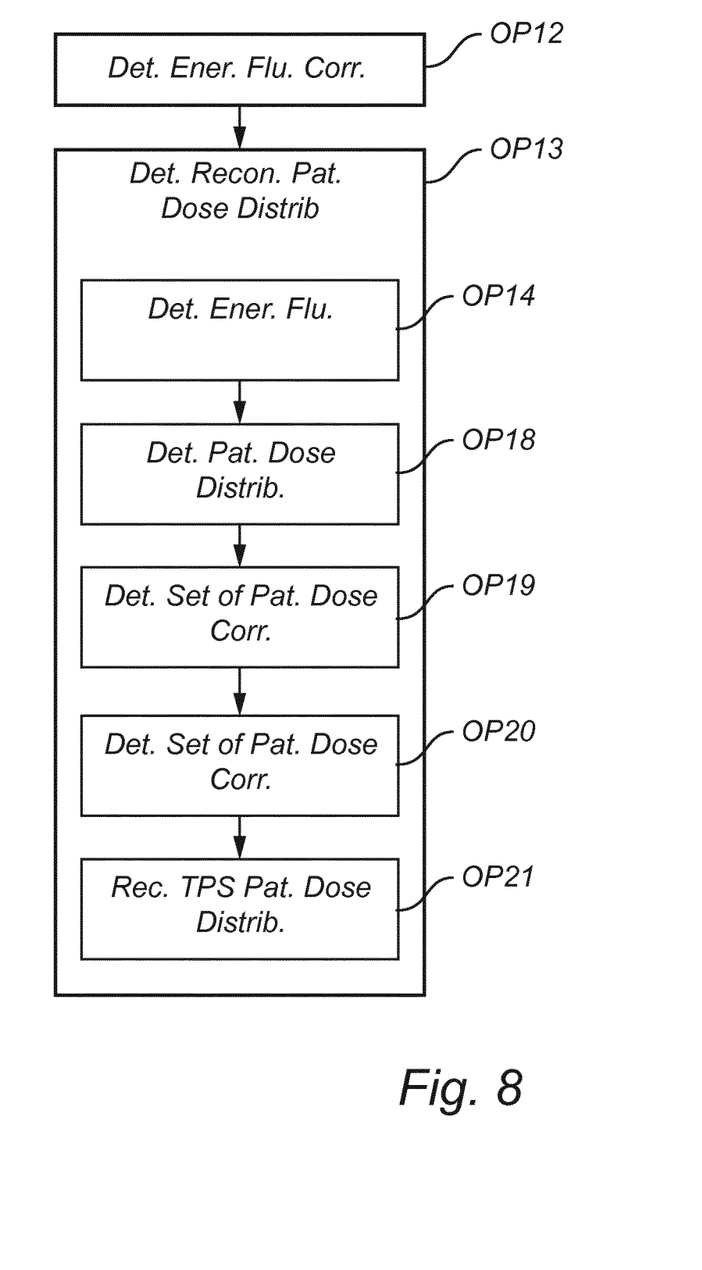

An alternative approach to the TPS patient dose distribution with absolute correction described above, is another embodiment, described with reference to FIG. 8, as follows. An inherent feature of this embodiment is that a relative dose correction is applied to the TPS patient dose distribution.

The operation of determining a reconstructed patient dose distribution, OP13, comprises determining a patient dose distribution on basis of the energy fluence and the patient description, wherein said further data related to the treatment plan description comprises the treatment planning system patient dose distribution, OP18; determining a set of patient dose corrections on basis of the energy fluence corrections and the patient description, OP19; determining a set of relative patient dose corrections on basis of the patient dose distribution and the set of patient dose corrections, OP20; receiving a TPS PDD, OP21, wherein said further data related to the treatment plan description comprises the TPS PDD; and determining the reconstructed patient dose distribution on basis of the set of relative patient dose corrections, and the TPS PDD.

For each subbeam, an energy fluence correction can be calculated from phantom dose measurements in any one of the above embodiments.

The internal patient dose and the patient dose correction are calculated with the same dose engine. Hence, the artefacts in the two dose distributions that originate in the dose model selection and implementation details should balance in the relative dose correction distribution.

As in the case for the absolutely corrected TPS patient dose, the relatively corrected dose is calculated on an appropriate subbeam level. The subbeam contributions are summed together to form a dose distribution on a level that is relevant to compare to the TPS patient dose. That is, beam or plan level.

Figure 9:
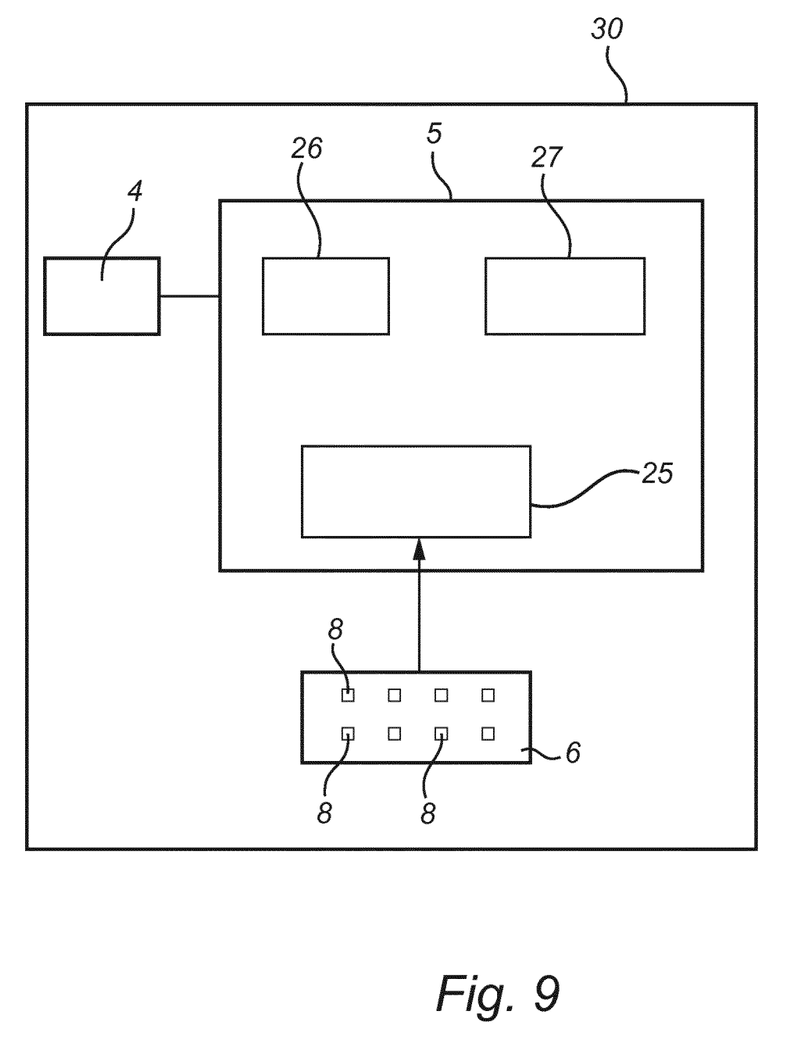
FIG. 9 is a block diagram of an embodiment of a control system according to the present invention.

As schematically illustrated in FIG. 9, an embodiment of a control system 30 for a radiation therapy treatment apparatus, comprises the treatment planning system 4 and the quality assurance system 5, 6 with the computing device 5 and the phantom 6. As mentioned above, the phantom 6 does not have to be a physical device but it can be a virtual phantom as well, i.e. a computational model for a phantom, which computational model is used for transforming radiation values measured somewhere downstream of the radiation device 3 to dose values at the phantom. The computing device 5 comprises a measuring module 25, which is connected with the radiation detectors 8, an input data device 26, and an output data device 27. The input data device 26 is arranged to receive a treatment plan description from the TPS 4. The output data device 27 is arranged to output the final reconstructed patient dose distribution. The control system in general, and the QA system in particular, are arranged to perform the embodiments of the methods described above. As an optional function, the computing device 5 is arranged to determine whether the difference between the reconstructed patient dose distribution differs beyond a threshold from the desired, i.e. intended, patient dose distribution that the treatment plan was designed to provide, or not. The output data device outputs an indication of whether the difference is below the threshold or not, as a way to give an operator a quick indication of the result of the verification.

As is understood by a person skilled in the art, at least some of the above-described parts of the QA system can be implemented either as hardware components or as software, i.e. as computer readable instructions, which are executed by a processor of the QA system, such as the computing device 5. The operation of the above methods can be implemented by a computer program as well, i.e. by computer readable instructions, which when executed by a computing system causes the computing system to perform the method.

It should be noted that even if not explicitly expressed above, the method according to this invention can be performed during treatment of a patient as well. Then a virtual phantom is particularly applicable.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for determining an energy fluence correction in a quality assurance system for a radiation therapy apparatus, comprising:
 receiving a treatment plan description;
 generating a set of measured phantom dose values;
 generating a set of determined phantom dose values by determining phantom dose values on basis of at least the treatment plan description and a phantom description, wherein said generating the set of determined phantom dose values further comprises:
  determining an energy fluence on basis of the treatment plan description, and
  using the energy fluence for said determination of the phantom dose values;
 determining a set of phantom dose corrections on basis of at least the set of determined phantom dose values and the set of measured phantom dose values; and
 determining the energy fluence correction by an inverse dose calculation on basis of at least the set of phantom dose corrections.

2. The method according to claim 1, further comprising:
 receiving, at the quality assurance system, a set of treatment planning system phantom dose values, determined by a treatment planning system, wherein said determining the set of phantom dose corrections is further based on the set of treatment planning system phantom dose values.

3. The method according to claim 2, wherein said determining the set of phantom dose corrections comprises:
 determining a first set of phantom dose differences on basis of the set of determined phantom dose values and the set of measured phantom dose values;
 determining a second set of phantom dose differences on basis of the set of determined phantom dose values and the set of treatment planning system phantom dose values; and
 combining the first set of phantom dose differences with the second set of phantom dose differences.

4. The method according to claim 2, wherein said generating the set of determined phantom dose values comprises:
 determining the energy fluence on basis of the treatment plan description, wherein said determination of the phantom dose values is based on the energy fluence.

5. The method according to claim 2, wherein the energy fluence correction is generated based on the inverse dose calculation.

6. The method according to claim 1, wherein said generating the set of determined phantom dose values comprises:
 determining the energy fluence on basis of the treatment plan description, wherein said determination of the phantom dose values is based on the energy fluence.

7. The method according to claim 1, wherein the energy fluence correction is generated based on the inverse dose calculation.

8. A method for determining a reconstructed patient dose distribution comprising:
 determining an energy fluence correction in a quality assurance system for a radiation therapy apparatus comprising:
  receiving a treatment plan description,
  generating a set of measured phantom dose values,
  generating a set of determined phantom dose values, by determining phantom dose values on basis of at least the treatment plan description and a phantom description, wherein generating the set of determined phantom dose values further comprises:
   determining an energy fluence on basis of the treatment plan description, and
   using the energy fluence for said determination of the phantom dose values,
  determining a set of phantom dose corrections on basis of at least the set of determined phantom dose values and the set of measured phantom dose values, determining the energy fluence correction by an inverse dose calculation on basis of at least the set of phantom dose corrections; and determining the reconstructed patient dose distribution on basis of at least the energy fluence correction, a patient description, and further data related to the treatment plan description.

9. The method according to claim 8, wherein said determining the reconstructed patient dose distribution comprises:

determining the energy fluence on basis of said treatment plan description, wherein said further data related to the treatment plan description comprises the energy fluence.

10. The method according to claim 9, wherein said determining the reconstructed patient dose distribution comprises:

determining a corrected energy fluence based on the energy fluence correction and the energy fluence; and determining the reconstructed patient dose distribution based on the corrected energy fluence and the patient description.

11. The method according to claim 9, wherein said determining the reconstructed patient dose distribution comprises:

determining a patient dose distribution on basis of the energy fluence and the patient description, wherein said further data related to the treatment plan description comprises the patient dose distribution;

determining a set of patient dose corrections on basis of the energy fluence correction and the patient description;

determining a set of relative patient dose corrections on basis of the patient dose distribution and the set of patient dose corrections;

receiving a treatment planning system patient dose distribution, wherein said further data related to the treatment plan description comprises the treatment planning system patient dose distribution; and determining the reconstructed patient dose distribution on basis of the set of relative patient dose corrections.

12. The method according to claim 11, wherein the set of patient dose corrections constitutes a dose correction distribution in a patient geometry, the patient dose distribution constitutes an ideal dose distribution in the patient geometry, and the set of relative patient dose corrections constitutes a relative dose correction in a patient volume.

13. The method according to claim 11, wherein said determining the reconstructed patient dose distribution comprises:

determining the set of patient dose corrections on basis of at least the energy fluence correction and the patient description;

receiving said further data related to the treatment plan description in the form of the treatment planning system patient dose distribution; and determining the reconstructed patient dose distribution on basis of at least the treatment planning system patient dose distribution and the set of patient dose corrections.

14. A quality assurance system for a radiation therapy treatment apparatus, comprising:

a phantom to simulate a radiation therapy treatment, wherein the phantom is provided with radiation detectors; and a computing device comprising:

a measuring module connected with the radiation detectors, wherein the measuring module is configured to generate a set of measured phantom dose values, an input data device, wherein the input data device is configured to receive a treatment plan description, and an output data device;

wherein the computing device is configured to:

generate a set of determined phantom dose values by determining phantom dose values on basis of at least the treatment plan description and a phantom description, wherein to generate the set of determined phantom dose values further comprises:

determine an energy fluence on basis of the treatment plan description, and use the energy fluence for said determination of the phantom dose values;

determine a set of phantom dose corrections on basis of at least the set of determined phantom dose values and the set of measured phantom dose values; and determine an energy fluence correction by an inverse dose calculation on basis of at least the set of phantom dose corrections.

15. The quality assurance system according to claim 14, wherein the computing device is configured to determine a reconstructed patient dose distribution on basis of at least the energy fluence correction, a patient description, and further data related to the treatment plan description; and wherein the output data device is configured to output the reconstructed patient dose distribution.

* * * * *